US008886500B2

(12) United States Patent
De Backer

(10) Patent No.: US 8,886,500 B2
(45) Date of Patent: Nov. 11, 2014

(54) METHOD FOR DETERMINING TREATMENTS USING PATIENT-SPECIFIC LUNG MODELS AND COMPUTER METHODS

(75) Inventor: Jan De Backer, Brussel (BE)

(73) Assignee: Fluidda Respi, Kontich (BG)

( * ) Notice: Subject to any disclaimer, the term of this patent is extended or adjusted under 35 U.S.C. 154(b) by 348 days.

(21) Appl. No.: 13/322,104

(22) PCT Filed: May 27, 2010

(86) PCT No.: PCT/EP2010/057328
§ 371 (c)(1),
(2), (4) Date: Nov. 22, 2011

(87) PCT Pub. No.: WO2010/136528
PCT Pub. Date: Dec. 2, 2010

(65) Prior Publication Data
US 2012/0072193 A1    Mar. 22, 2012

Related U.S. Application Data

(60) Provisional application No. 61/182,493, filed on May 29, 2009.

(30) Foreign Application Priority Data

May 29, 2009  (EP) ..................... 09161455

(51) Int. Cl.
| G06F 7/48 | (2006.01) |
| G06F 19/00 | (2011.01) |
| A61M 16/00 | (2006.01) |
| A61B 5/085 | (2006.01) |

(52) U.S. Cl.
CPC ....... *A61M 16/00* (2013.01); *A61M 2210/1039* (2013.01); *G06F 19/3437* (2013.01); *A61B 5/085* (2013.01)
USPC ........................................................... 703/6

(58) Field of Classification Search
None
See application file for complete search history.

(56) References Cited

U.S. PATENT DOCUMENTS 8,573,205 B2 * 11/2013 Habashi ................... 128/204.23
2004/0009459 A1   1/2004 Anderson et al.
(Continued)

FOREIGN PATENT DOCUMENTS

WO   WO 92/04860    4/1992
WO   WO 01/56491    8/2001
(Continued)

OTHER PUBLICATIONS

Kabilan et al., "Characteristics of airflow in a CT-based ovine lung: a numerical study", J Appl Physiol 102 (4), Apr. 2007, pp. 1469-1482.*
(Continued)

*Primary Examiner* — Thai Phan
*Assistant Examiner* — Herng-Der Day
(74) *Attorney, Agent, or Firm* — Knobbe, Martens, Olson & Bear, LLP

(57) ABSTRACT

The disclosure relates to determining optimized parameters for mechanical ventilation comprising: obtaining data concerning a three-dimensional image of the subject's respiratory system; calculating a specific three-dimensional structural model of the subject's lung structure from the image data; calculating a specific three-dimensional structural model of the subject's airway structure from the image data; calculating a patient-specific three-dimensional structural model of the subject's lobar structure from the lung model; modeling the air flow through the airway, using the models of the airway and lobar structure of the subject at defined MV parameters; modeling the structural behavior of the airway and the interaction with the flow, using the models of the airway and lobar structure of the subject at defined MV parameters; determining the MV parameters which lead to a decrease in airway resistance and hence an increase in lobar mass flow for the same driving pressures according to the model.

10 Claims, 13 Drawing Sheets

(56) References Cited

U.S. PATENT DOCUMENTS

Figure 1A:
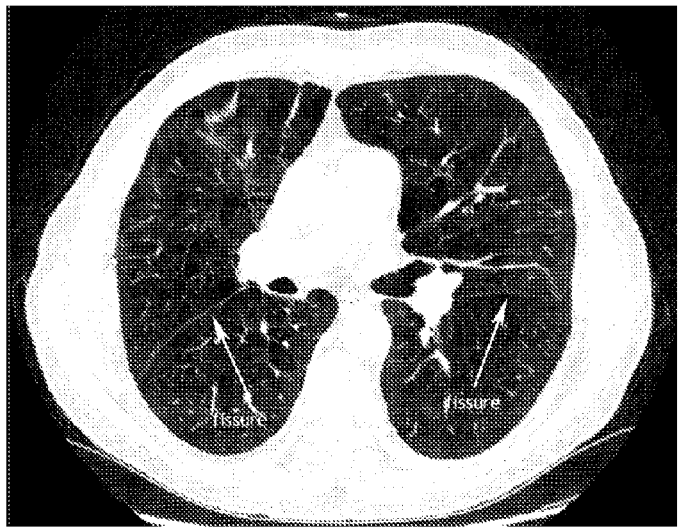

2007/0000494 A1 1/2007 Banner et al.
2007/0156453 A1 7/2007 Frielinghaus et al.
2011/0093243 A1* 4/2011 Tawhai et al. .................... 703/2

FOREIGN PATENT DOCUMENTS

WO   WO 2004/019766   3/2004
WO   WO 2007/059477   5/2007

OTHER PUBLICATIONS

Wall et al., "Fluid-structure interaction in lower airways of CT-based lung geometries", International Journal for Numerical Method in Fluids, vol. 57, Issue 5, Jun. 2008, pp. 653-675.*

De Backer, et al. "Flow Analyses in the Lower Airways: Patient-specific Model and Boundary Conditions," *Medical Engineering & Physics*, vol. 30, No. 7, pp. 872-879, Sep. 1, 2008.

International Search Report dated Sep. 30, 2010, issued to international application No. PCT/EP2010/057328.

* cited by examiner

US 8,886,500 B2

METHOD FOR DETERMINING TREATMENTS USING PATIENT-SPECIFIC LUNG MODELS AND COMPUTER METHODS

CROSS-REFERENCE TO RELATED APPLICATIONS

This application is the U.S. National Phase under 35 U.S.C. §371 of International Application PCT/EP2010/057328, filed May 27, 2010, which claims priority to EP 09161455.2, filed May 29, 2009 and U.S. Provisional Application No. 61/182,493, filed May 29, 2009.

FIELD OF THE INVENTION

The present invention is in the field of mechanical ventilators (MVs), and determining efficacy of treatment for respiratory-type conditions. Particularly, it is in the field of determining optimized parameters for operating MVs.

BACKGROUND TO THE INVENTION

Mechanical ventilation is a method to mechanically assist or replace natural breathing in a subject.

Mechanical airway ventilation (MV) of a subject/patient can be subdivided into two major categories: invasive (IV) and non-invasive ventilation (NW). Invasive ventilation uses an endrotracheal tube or tracheotomy to restore alveolar ventilation and gas exchange. NW is used to provide patients with respiratory support through a mask without the invasive nature of an intubation or tracheotomy (Kinnear W J M. Non-Invasive Ventilation Made Simple. Nottingham University Press, 2007). Ventilation entails a range of medical ventilator support techniques such as, but not limited to Continuous Positive Airway Pressure (CPAP), Non-invasive Positive Pressure Ventilation (NIPPV), Bi-Level Positive Airway Pressure (BiPAP), Intrapulmonary percussive ventilation (IPV), and Mechanical Insufflator-Exsufflator.

IPV and Mechanical Insufflator-Exsufflator techniques are mainly used in physiotherapy to improve the patient's breathing through the removal of excessive mucus.

IV is usually applied to patients that cannot breathe independently, typically in an intensive care unit. The respirator provides respiratory flow often without the requirement for patient effort. Pressure and volume controlled modi can be used and the patient can in some settings still trigger the ventilator. NIV on the other hand can offer the same support (also completely volume controlled or pressured controlled with or without back-up volume) but mostly patients still trigger the ventilator. NIV is often used in patients with restrictive neuromuscular diseases such as amyotrophic lateral sclerosis (ALS), myotonic dystrophy (Steinert's disease), Duchenne muscular dystrophy, Acid maltase deficiency, and Emery-Dreifuss myopathy.

Recently, NIV has been used increasingly in chronic obstructive pulmonary disease (COPD) patients. Recent studies indicate that NIV in COPD can have a beneficial effect although the data are not always conclusive (Dreher M, Kenn K and Windisch W. Non-invasive ventilation and physical exercise in patients with COPD. *Pneumologie* 62: 162-168, 2008; McEvoy R D, Pierce R J, Hillman D, Esterman A, Ellis E E, Catcheside P G, O'Donoghue F J, Barnes D J and Grunstein R R. Nocturnal Non-Invasive Nasal Ventilation in Stable Hypercapnic COPD: A Randomised Controlled Trial. *Thorax* 2009; Windisch W, Haenel M, Storre J H and Dreher M. High-intensity non-invasive positive pressure ventilation for stable hypercapnic COPD. *Int J Med Sci* 6: 72-76, 2009).

It is the general impression that a subset of the patient population may benefit significantly from NIV, while the effect is less pronounced in other patients.

With a mechanical ventilator, several parameters must be adjusted according to the patient needs, including, for instance, pressure, volume of gas, respiratory rate, rise time, I:E ratio, trigger mode and sensitivity. The correct parameters are necessary to restore alveolar ventilation, prevent atelectasis, and optimize gas exchange. Moreover, MV carries many potential complications including pneumothorax, airway injury, alveolar damage, and ventilator-associated pneumonia. For this reason the settings of the MV must be carefully determined. Typically the adjustments of the ventilator settings are still empirical, using the obtained gas exchange reflected in blood gas analysis, oxygen saturation and $CO_2$ monitoring as guidance.

The aim of the present invention is to optimize the setting of the parameters for MV, which allows more subsets of the population to benefit, and also to reduce treatment failures due to an excessively long or inadequate start up period.

SUMMARY OF SOME EMBODIMENTS OF THE INVENTION

One embodiment of the invention is a method for determining optimised parameters for mechanical ventilation, MV, of a subject, comprising:
a) obtaining data concerning a three-dimensional image of the subject's respiratory system,
b) calculating a specific three-dimensional structural model of the subject's lung structure from the image data obtained in step a),
c) calculating a specific three-dimensional structural model of the subject's airway structure from the image data obtained in step a),
d) calculating a patient-specific three-dimensional structural model of the subject's lobar structure from the lung model obtained in step b),
e) modeling by a computer, the air flow through the airway, using the models of the airway and lobar structure of the subject obtained in steps c) and d) at defined MV parameters;
f) modeling by a computer, the structural behavior of the airway and the interaction with the flow, using the models of the airway and lobar structure of the subject obtained in steps b) and c) at defined MV parameters;
g) determining the MV parameters which lead to a decrease in airway resistance and hence an increase in lobar mass flow for the same driving pressures according to the model of step d), thereby obtaining optimized MV parameters.

Another embodiment of the invention is a method as described above, wherein the image data of step a) is previously obtained using a CT or MRI scan.

Another embodiment of the invention is a method as described above, wherein the structural model of step c) is calculated using segmentation principles.

Another embodiment of the invention is a method as described above, wherein the model of step d) is calculated using lobar segmentation.

Another embodiment of the invention is a method as described above, wherein the modeling of step e) comprises computational fluid dynamics incorporating solving the Navier-Stokes equations numerically.

Another embodiment of the invention is a method as described above, wherein the lobar structure determined in step d) is used to determine boundary conditions for computational fluid dynamics.

Another embodiment of the invention is a method as described above, wherein the data of step a) concerns three dimensional images of the respiratory system at total lung capacity, TLC and at functional residual capacity, FRC, model of the lung structure in step b) and model of the lobar structure in step d) are calculated both at TLC and FRC, to determine mass flow rate towards each lobe and subsequently the boundary conditions for said computational fluid dynamics.

Another embodiment of the invention is a method as described above, wherein the modeling of step f) comprises Finite Element Analysis, FEA.

Another embodiment of the invention is a method for assessing the efficacy of a treatment for a respiratory condition in a subject comprising the steps of:

a) obtaining data concerning a pre-treatment three-dimensional image of the subject's respiratory system, and a post-treatment three-dimensional image of the subject's respiratory system, b) calculating a specific three-dimensional structural model of the subject's lung structure from each of the pre- and post-treatment image data obtained in step a), c) calculating a specific three-dimensional structural model of the subject's airway structure from each of the pre- and post-treatment image data obtained in step a), d) calculating a patient-specific three-dimensional structural model of the subject's lobar structure from each of the pre- and post-treatment lung structure models obtained in step b), e) modeling by a computer, the air flow through the airway at pre- and post-treatment states, using the respective pre- and post-treatment models of the airway and lobar structure of the subject obtained in steps c) and d);

f) modeling by a computer, the structural behavior of the airway and the interaction with the flow at pre- and post-treatment states, using the respective pre- and post-treatment models of the airway and lobar structure of the subject obtained in steps c) and d);

g) comparing the modeled airflow and structural behaviour pre- and post-treatment to determine the efficacy of a treatment.

Another embodiment of the invention is a method for assessing the efficacy of a treatment for a respiratory condition as described above, including any of the limitations of the method for determining optimised parameters as described above.

FIGURE LEGENDS

Figure 1B:
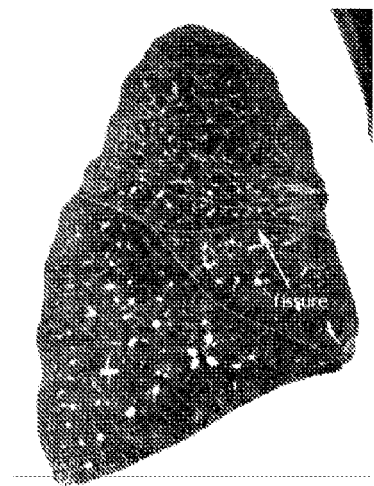

FIGS. 1A and B: CT scan through the thorax of a subject with fissure lined indicated, used to determine division of lung lobes in the lobar segmentation step. FIG. 1A shows transverse cross section while FIG. 1B shows longitudinal cross-section.

Figure 2A:
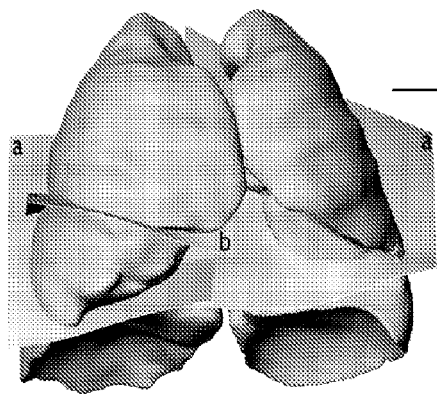
Figure 2B:
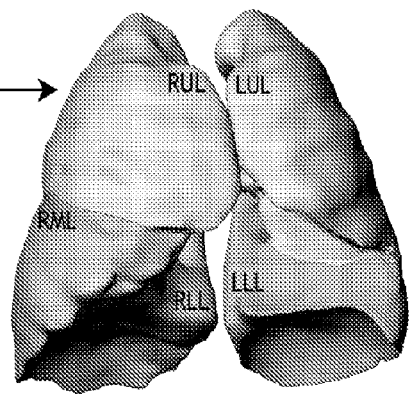

FIG. 2: Conversion of fissure lines in FIG. 1 to cutting planes (left) that can subdivide the lungs into their respective lobar volumes RUL (Right Upper Lobe), RML (Right Middle Lobe), RLL (Right Lower Lobe), LUL (Left Upper Lobe), LLL (Left Lower Lobe) (right).

Figure 3:
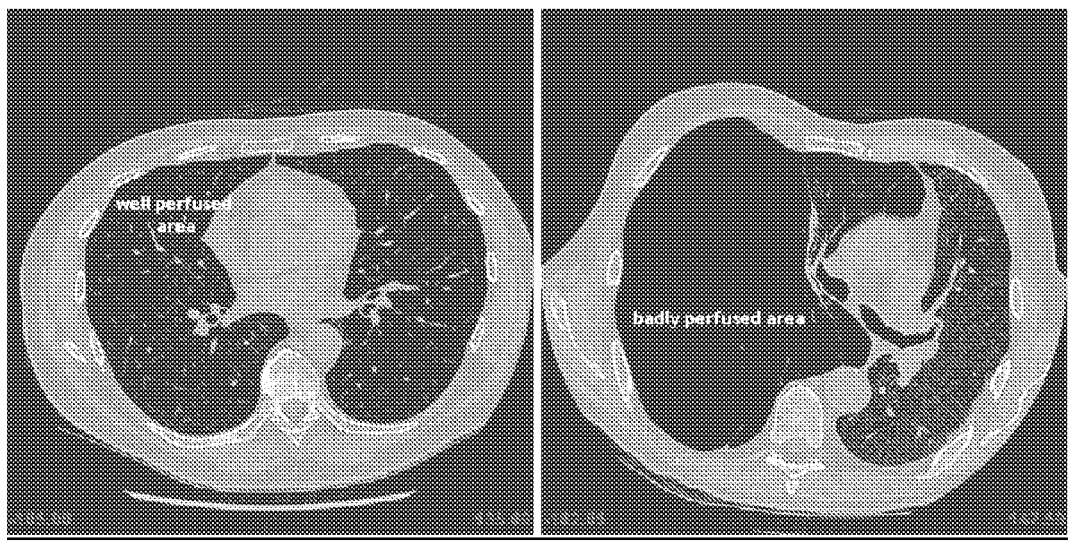

FIG. 3: CT scan through the thorax of a subject, showing well-perfused areas (left) and poorly-perfused areas (right) of the lung.

Figure 4:
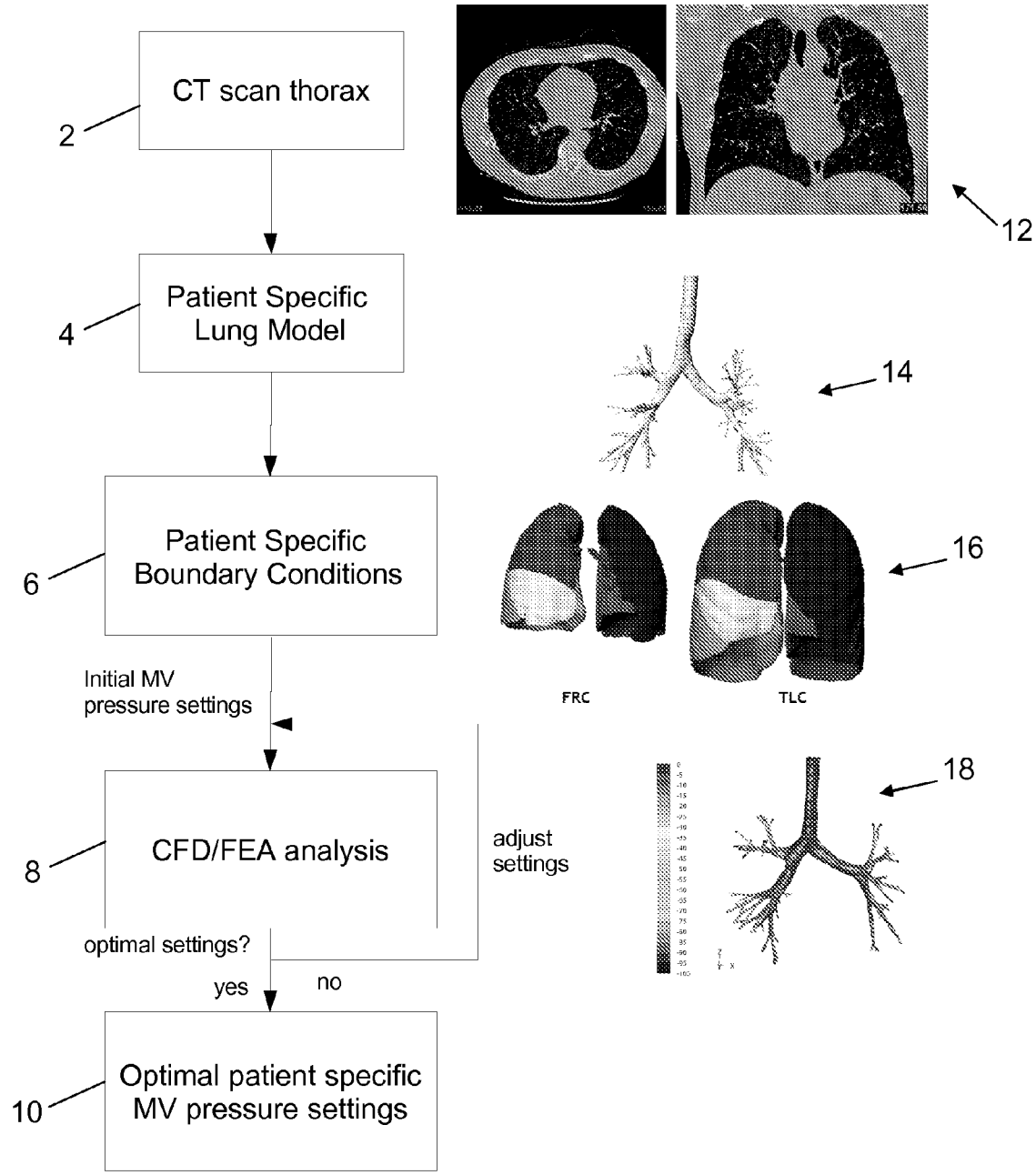

FIG. 4: Flow chart illustrating an embodiment of the method of the invention as a flow chart.

Figure 5:
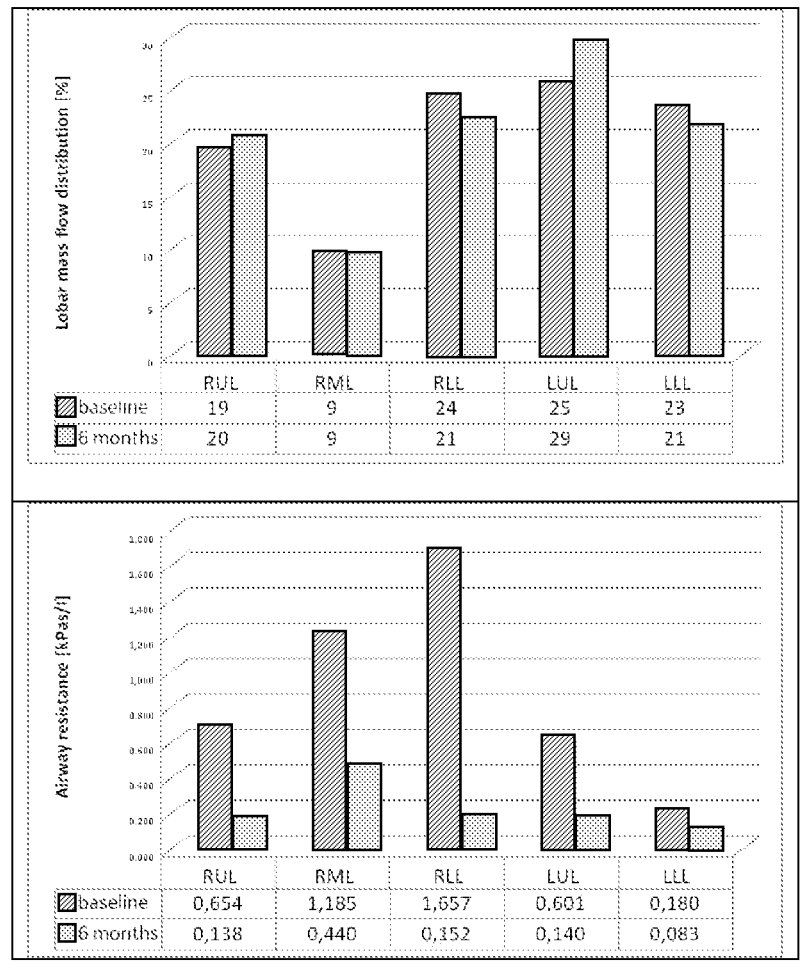

FIG. 5: Patient 1: change in mass flow distribution and airway resistance after NIV treatment (hatched=baseline; dotted=post NIV)—Control Patient.

Figure 6:
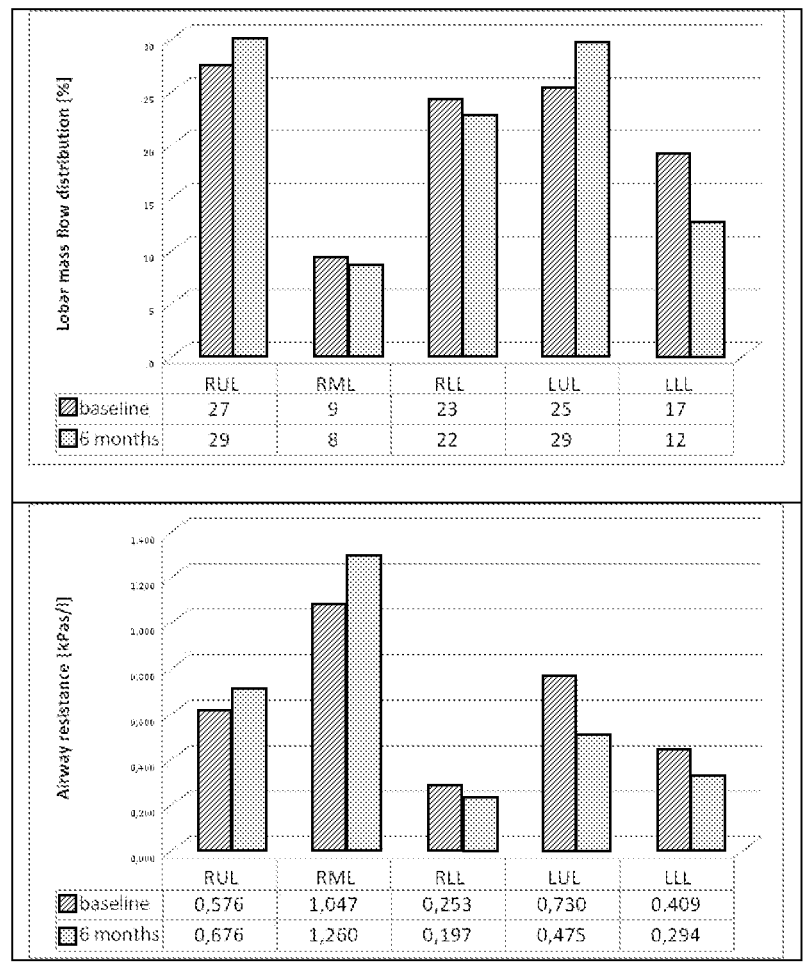

FIG. 6: Patient 2: change in mass flow distribution and airway resistance after NIV treatment (hatched=baseline; dotted=post NIV)—NIV patient.

Figure 7:
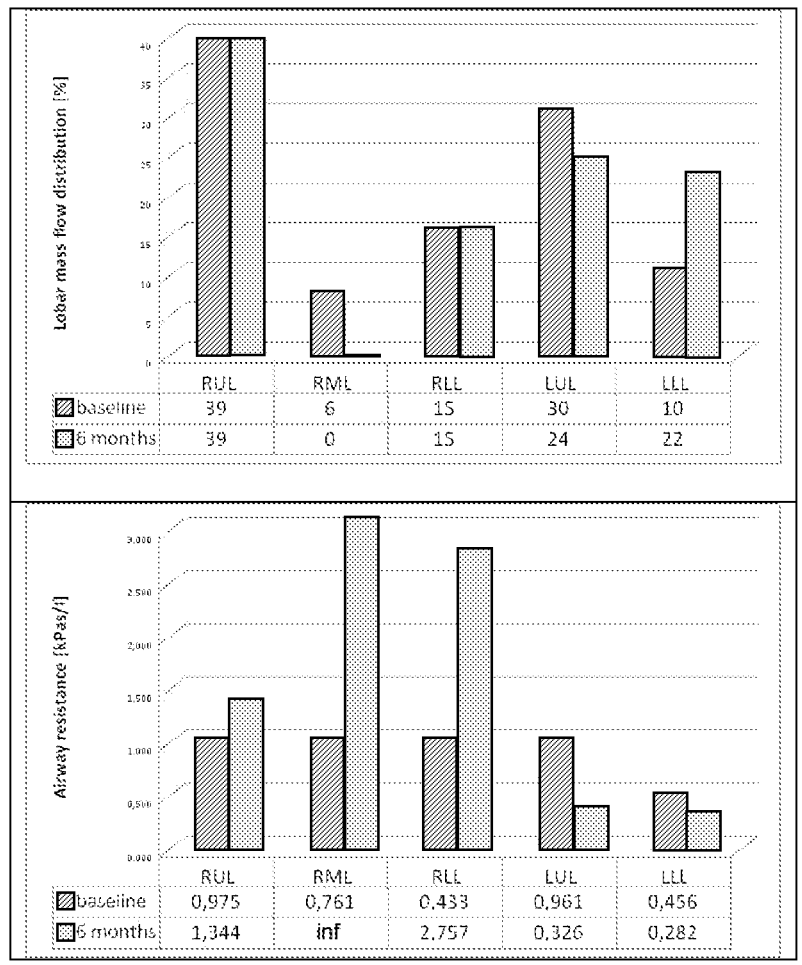

FIG. 7: Patient 3: change in mass flow distribution and airway resistance after NIV treatment (hatched=baseline; dotted=post NIV)—NIV patient.

Figure 8:
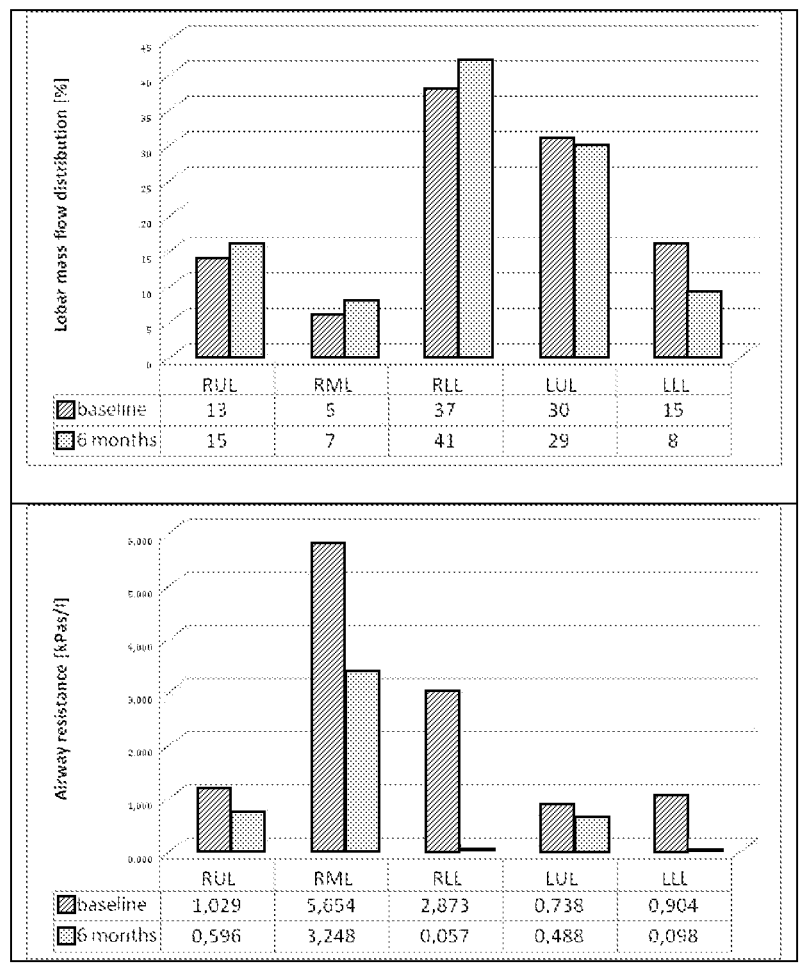

FIG. 8: Patient 4: change in mass flow distribution and airway resistance after NIV treatment (hatched=baseline; dotted=post NIV)—NIV patient.

Figure 9:
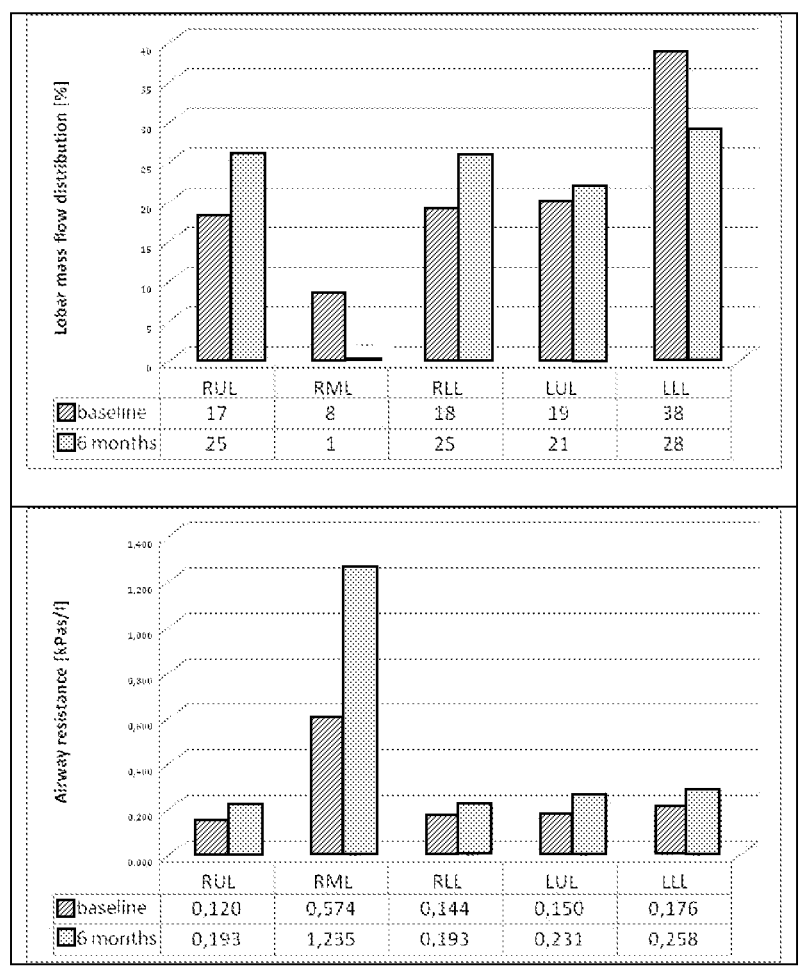

FIG. 9: Patient 5: change in mass flow distribution and airway resistance after NIV treatment (hatched=baseline; dotted=post NIV)—NIV patient.

Figure 10:
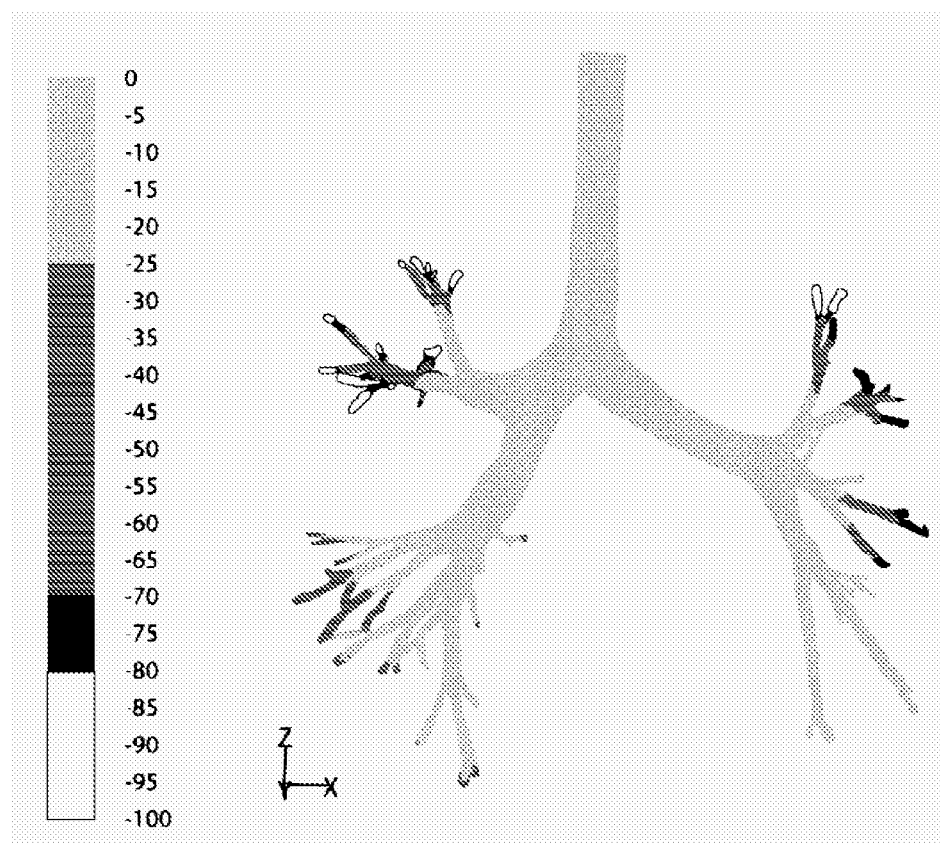

FIG. 10: Static pressure distribution in patient specific airway model.

Figure 11:
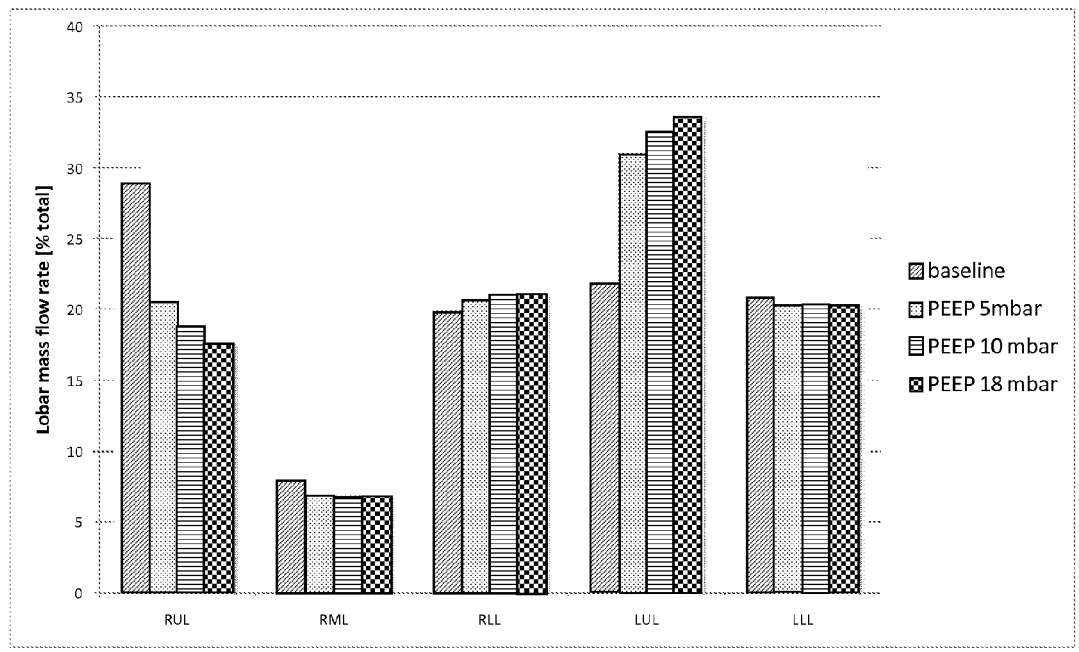

FIG. 11: Lobar mass flow distribution as a function of Peak End Expiratory Pressure (PEEP).

Figure 12:
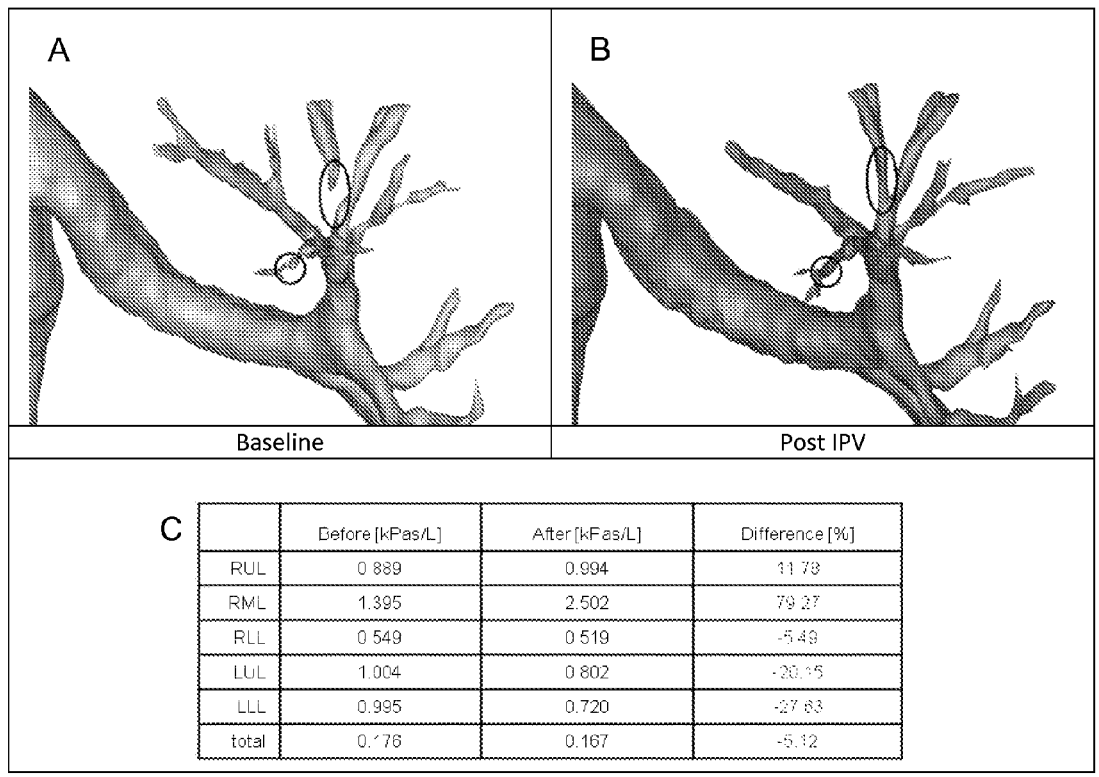

FIG. 12: Patient 1: effect of IPV treatment on airway morphology and resistance.

Figure 13:
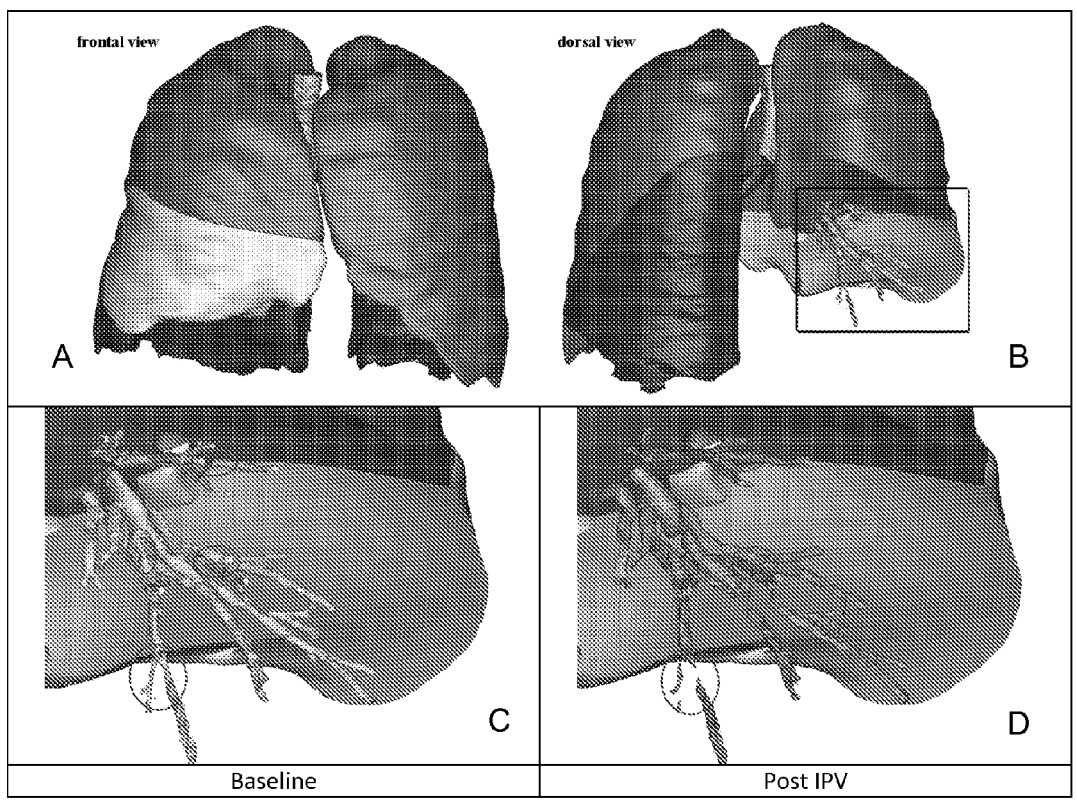

FIG. 13: Patient 2: effect of IPV treatment on airway morphology.

Figure 14:
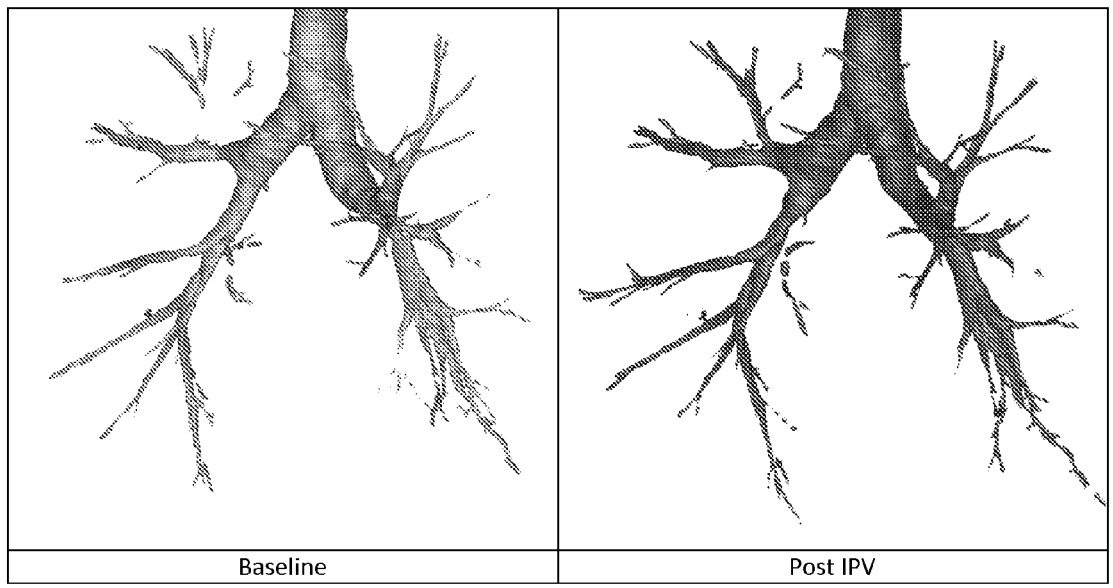

FIG. 14: Patient 3: effect of IPV treatment on airway morphology.

Figure 15:
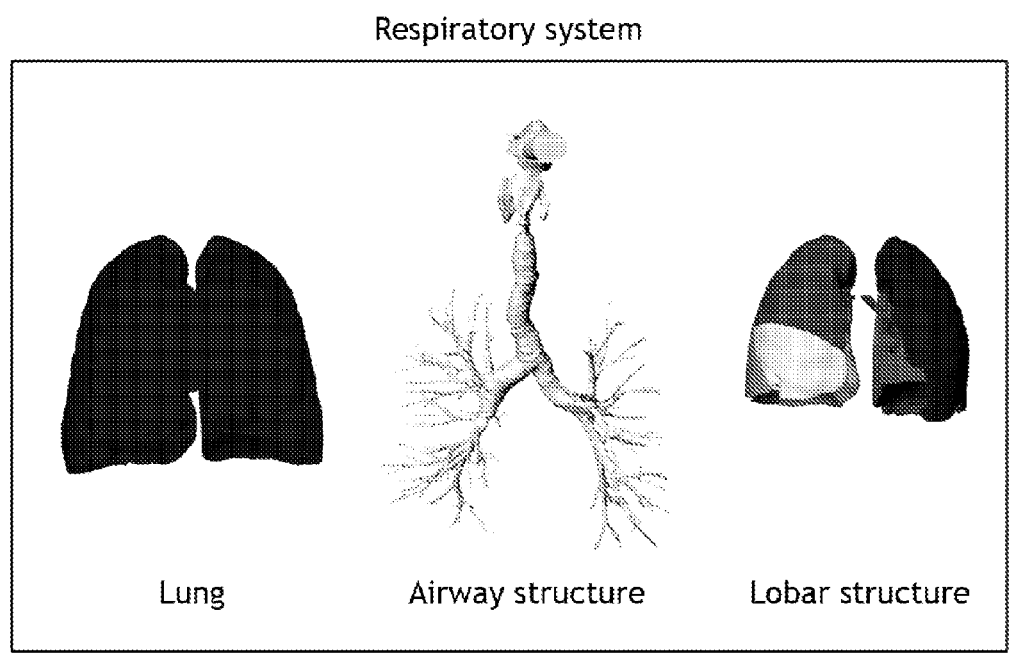

FIG. 15: Structural models of the lung (left), airway (middle) and lobar (right) structure, generated by the invention.

Figure 16:
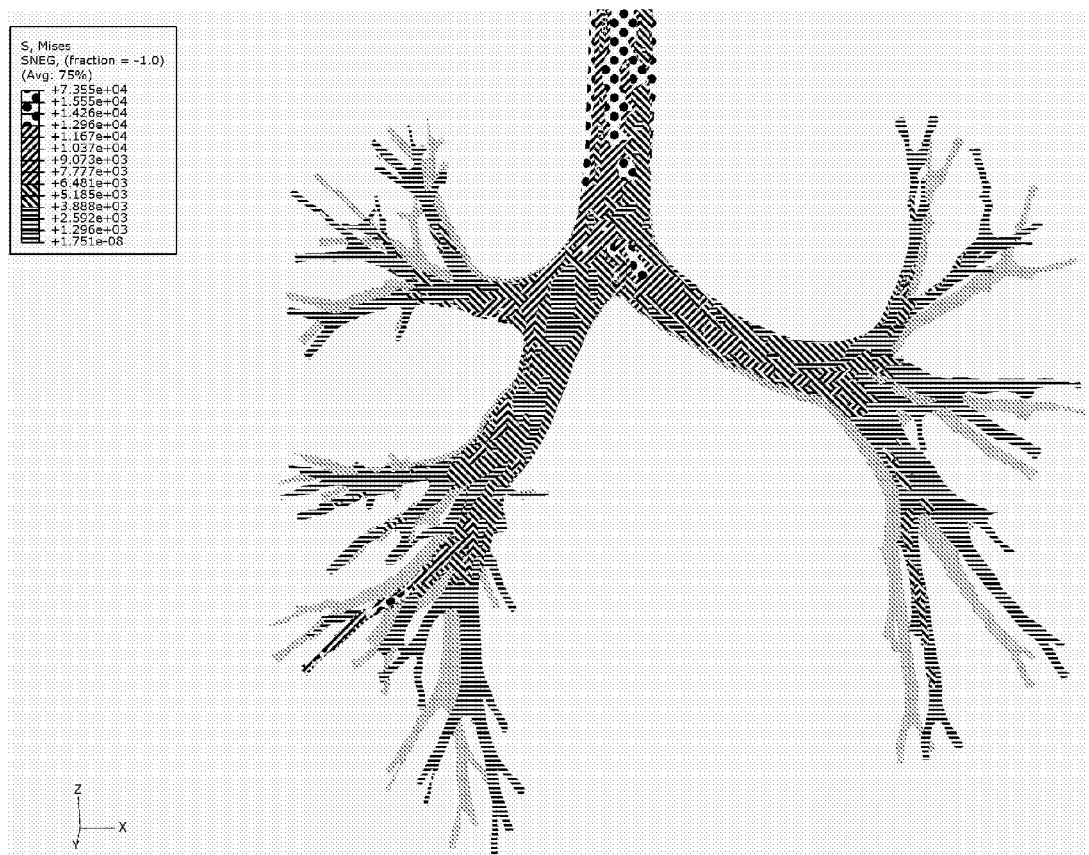

FIG. 16: A structure behaviour model of the airways, wherein the grey model indicated the original position of the model, and the displaced, shaded model depicts calculated stresses.

DETAILED DESCRIPTION OF THE INVENTION

The present invention concerns a method to determine the parameters for mechanical airway ventilation (MV) of a specific subject, comprising modeling of the air flow through the upper airway of a subject suffering from respiratory insufficiency.

The present invention concerns a method for optimising the parameters setting for mechanical airway ventilation (MV) of a specific subject comprising the steps of:

a) obtaining data concerning a three-dimensional image of the subject's respiratory system, b) calculating a specific three-dimensional structural model of the subject's lung structure from the image data obtained in step a), c) calculating a specific three-dimensional structural model of the subject's airway structure from image data obtained in step a), d) calculating a patient-specific three-dimensional structural model of the subject's lobar structure from the lung structure model obtained in step b), e) modeling by a computer, the air flow through the airway, using the models of the airway and lobar structure of the subject obtained in steps c) and d) at defined MV parameters;

f) modeling by a computer, the structural behavior of the airway and the interaction with the flow, using the models of the airway and lobar structure of the subject obtained in steps c) and d) at defined MV parameters;

g) determining the MV parameters (of steps e) and f)) which lead to a decrease in airway resistance hence an increase in lobar mass flow for the same driving pressures according to the model of step d), thereby obtaining optimized MV parameters.

Starting with a structural model of the respiratory system of the subject, and applying computational fluid dynamics (CFD), the present invention produces a set of parameters that are specific to the airway geometry of the subject, and which have the effect of improving alveolar ventilation, i.e. to decrease the $pCO_2$ tension in the blood. The optimized parameters preferably lead to alveolar opening and adequate pressure to prevent early expiratory airway closing and built up of iPEEP with corresponding hyperinflation.

The present invention also concerns a method for assessing the efficacy of a treatment for a respiratory-type condition in a subject comprising the steps of:

a) obtaining data concerning a pre-treatment three-dimensional image of the subject's respiratory system, and a post-treatment three-dimensional image of the subject's respiratory system, b) calculating a specific three-dimensional structural model of the subject's lung structure from each of the pre- and post-treatment image data obtained in step a), c) calculating a specific three-dimensional structural model of the subject's airway structure from each of the pre- and post-treatment image data obtained in step a), d) calculating a patient-specific three-dimensional structural model of the subject's lobar structure from each of the pre- and post-treatment lung structure models obtained in step b), e) modeling by a computer, the air flow through the airway at pre- and post-treatment states, using the respective pre- and post-treatment models of the airway and lobar structure of the subject obtained in steps c) and d);

f) modeling by a computer, the structural behavior of the airway and the interaction with the flow at pre- and post-treatment states, using the respective pre- and post-treatment models of the airway and lobar structure of the subject obtained in steps c) and d);

g) comparing the modeled airflow (step e) and structural behaviour (step f) pre- and post-treatment to determine the efficacy of a treatment.

The treatment for a respiratory condition may be the administration of a medicament (e.g. Salbutamol) or MV of the art or MV as described herein. Preferably, an efficacious treatment is one that decreases the airway resistance thereby increasing the lobar mass flow for the same driving pressure.

The one embodiment of a method of the invention for optimising the parameters setting for MV of a specific subject is presented as a flow chart in FIG. 4. According to the embodiment, a CT scan of the thorax of the subject is taken 2, resulting in scan data 12. From the scan data 12, a patient specific lung model is generated 4, resulting in data concerning the geometry of the airways 14. Boundary specific conditions are calculated 6 using the scan data 12, resulting in data concerning the subject's lobar structure 16. CFD analysis is performed 8 using data concerning the geometry of the airways 14, the boundary conditions, and using initial MV parameters (e.g. pressure settings). Settings are adjusted iteratively until an optimized mass flow distribution is obtained 18. The optimal settings 10 are employed in the MV.

The present invention is suitable for the treatment of, or for monitoring the treatment of respiratory-type conditions. These conditions are any that result in reduced gaseous exchange, and include hypercapnic chronic obstructive pulmonary disease (COPD), asthma, cystic fibrosis (CF) and those which manifest as a result of other restrictive disorders, such as neuromuscular disorders that might include amyotrophic lateral sclerosis (ALS), myotonic dystrophy (Steinert's disease), Duchenne muscular dystrophy, Acid maltase deficiency, and Emery-Dreifuss myopathy.

The present invention provides subject-specific, optimized parameters for an MV. Examples of parameters include in and expiratory pressures, tidal volume to be delivered, respiration rate, I:E ratio, gas composition.

It is well understood in the art that the same MV can be utilised without adaptation for IV as well as for NIV. For an MV used in IV mode, ventilation is provided to the subject via an endrotracheal tube or tracheotomy; for an MV used in NIV mode, ventilation is provided to the subject via a mask. MV machines suitable for use with the present are any of the art, and include, for example, those manufactured by Drager, Siemens, Respironics, Resmed, Tyco, and Weinmann.

Data concerning three-dimensional images of the respiratory system of the subject is obtained in step a). The images may have been previously acquired using any method of the art. Such methods include magnetic resonance imaging, positron emission tomography and computer tomography (CT) imaging to name a few. The "respiratory system" refers to the intra- and extra thoracic airways and the lungs. Preferably, the images are acquired at two lung volumes; one at total lung capacity (TLC), the lung level attained after a deep inhalation, and one at functional residual capacity (FRC), the lung level after normal expiration.

From the image data, a three-dimensional structural model of the subject's lung is generated (step b). The structural model refers to an internal structural model, especially indicating tissue structures. Preferably, a lung structural model is generated at each of the two lung volumes (TLC and FRC). When the invention is applied to determining efficacy of treatment, image data and structural models of the lung are obtained prior to and after the start of treatment (e.g. at a 1, 2, 3, 4, 5, 6, 7, 8, 9, 10 11, 12 months interval just prior to treatment, or at regular 1, 2, 3, 4, 5, 6, 7, 8, 9, 10 11, 12 month intervals).

Using data obtained from the three dimensional image in step a), a specific three-dimensional model of the subject's airway structure is constructed (step c). The airway structure includes the intra- and extra thoracic airways. The airway structure is preferably constructed using segmentation principles. During the segmentation procedure, voxels (volume elements) of the same anatomical structure of interest are placed in a separate mask. This mask is used to reconstruct the airways in three dimensions. Segmentation principle is known in the art, and described, for example, in "Flow analyses in the lower airways: patient-specific model and boundary conditions" De Backer J W, Vos W G, Gorlé C D, Germonpré P, Partoens B, Wuyts F L, Parizel P M, De Backer W. Med Eng Phys. 2008 September; 30(7):872-9. Where appropriate, separate airway models are constructed at total lung capacity (TLC), and at functional residual capacity (FRC). When the invention is applied to determining efficacy of treatment, separate airway models are constructed from the lung models obtained prior to and after the start of treatment. Preferably, the airway model is generated at TLC, though an airway model generated at FRC may be used at any time when necessary, for instance, when it appears to be more accurate.

Using data obtained from the three dimensional lung model, a specific three-dimensional model of the subject's lobar volumes is constructed i.e. the lobar volumes are segmented based on the said lung model (step d). A normal human has five lung lobes, three on the right side (RUL, RML, RLL) and two on the left (LUL, LLL). Initially, the complete right and left lungs are segmented, then the fissure lines are identified. These lines indicate the division between the several lung lobes, and can be distinguished from the thorax model (see CT scans of FIG. 1). These lines are then converted into cutting planes that can subdivide the lungs into their respective lobar volumes (FIG. 2). Lobar segmentation may be performed manually or automatically.

Preferably, separate lobar volume models are constructed at total lung capacity (TLC), and at functional residual capacity (FRC). By performing the lobar segmentation at FRC and TLC level, it is possible to assess the patient specific mass flow rate towards each lobe. This data may be used as a boundary conditions in subsequent flow simulations i.e. Computational Fluid Dynamics (CFD).

When the invention is applied to determine the efficacy of treatment, separate lobar volume models are constructed from the lung models obtained prior to and after the start of treatment. This data may be used as boundary conditions in subsequent flow simulations (CFD) in the airways prior to and after the start of treatment.

The patient-specific three-dimensional models of the airways are used to determine the respiratory air flow using Computational Fluid Dynamics (CFD) (step e) and structural behavior of the respiratory system using Finite Element Analysis (FEA) (step f). CFD simulates the flow behavior in the specific three-dimensional airway structure model by solving the mathematical flow equations (Navier-Stokes equations) numerically (De Backer J W, Vanderveken O M, Vos W G, Devolder A, Verhulst S L, Verbraecken J A, Parizel P M, Braem M J, Van de Heyning P H and De Backer W A. Functional imaging using computational fluid dynamics to predict treatment success of mandibular advancement devices in sleep-disordered breathing. (*J Biomech* 40: 3708-3714, 2007; De Backer J W, Vos W G, Devolder A, Verhulst S L, Germonpre P, Wuyts F L, Parizel P M and De B W.

Computational fluid dynamics can detect changes in airway resistance in asthmatics after acute bronchodilation *J Biomech* 41: 106-113, 2008; De Backer J W, Vos W G, Verhulst S L and De B W. "Novel imaging techniques using computer methods for the evaluation of the upper airway in patients with sleep-disordered breathing: a comprehensive review". *Sleep Med Rev* 12: 437-447, 2008). Also the subsequent structural behavior of the respiratory system, the interaction with the flow and the remodeling is determined using a combination of CFD and FEA techniques. The structural behavior of the model is determined by solving the structural equations for stresses, stains, displacements etc. as explained the biomedical engineering handbook (The Biomedical Engineering Handbook by Joseph Bronzino, IEEE press) This analysis allows for an assessment of the change in airway geometry due to the pressure exerted on the walls. Examples of computed stresses and displacements can be found in FIG. 16 where the grey model represents the original position of the model and the stresses are depicted in the displaced model.

In performing CFD, the three-dimensional airway structure model is subdivided into a plurality of discrete elements. The collection of these elements is called a computational mesh or grid. In each of the grid nodes, the flow equations are solved. Preferably the airway model constructed at TLC is used, however, the FRC model can be used at any time when necessary, for example, when it appears to be more accurate.

With a large system such as a lung, solution of the flow equations is assisted by determining adequate boundary conditions to close the system of equations, which boundary conditions are determined using the specific three-dimensional model of the subject's lobar volumes as mentioned above. Boundary conditions are derived from the CT images by assessing the lobar expansion from FRC to TLC. This indicates the fraction of the inhaled air that goes to each lobe for that specific patient. To make the models as accurate as possible, this patient-specific information may be reflected in the flow simulations. In practice, this may be achieved by adjusting the pressures at the bronchioli outlets to such an extent that the model mass flow rate is identical to the mass flow rate obtained via CT images.

To establish the baseline respiratory case, i.e. the situation of normal breathing without any respiratory support, the boundary conditions consist of a definition of mass flow rate at the mouth or trachea and pressure at the bronchioli. The pressures are iteratively determined to attain the mass flow rate towards each lobe corresponding to the CT-based lobar growth (De Backer J W, Vos W G, Gorle C D, Germonpre P, Partoens B, Wuyts F L, Parizel P M and De B W. Flow analyses in the lower airways: patient-specific model and boundary conditions. *Med Eng Phys* 30: 872-879, 2008).

Once the baseline case has been established, the pressure at the mouth or trachea is elevated to the level of non-invasive ventilatory pressure using CFD applied to the three-dimensional structural model of the subject's airway. The internal mass flow rate will adapt accordingly, and the local pressure on the airway wall can be determined by CFD as a function of MV settings. The structural response of the airways, remodeling and the interaction with the flow is then determined using FEA.

The aim of MV in COPD patients is mainly to decrease the $pCO_2$ levels in the blood at safe levels of gas pressure, volume and other parameters. This is done by increasing the ventilation towards better perfused areas such that alveolar ventilation increases and the gas exchange of $CO_2$ and $O_2$ is improved (FIG. 3). The MV parameters should, therefore, be set such that the pressure "opens up" the airways towards the well-perfused areas and the mass flow rate towards these areas increases.

The appropriate parameters can be determined by titrating the model with different MV parameters, and observing the appropriate effect using the airflow (CFD) and structural behaviour (FEA) models. Iterations of adjusting each MV parameter and observing the effect in the simulations is continued until an optimized set of MV parameters is found. In other words, steps e) and f) are repeated with different MV parameters until there a decrease in airway resistance hence an increase in lobar mass flow for the same driving pressures according to the model of step d). Because a patient-specific structural model is acquired at the start of the process, there is no need for high patient involvement, and the patient can benefit immediate from optimized and safe ventilation from the outset of treatment.

While lobar mass flow distribution is mainly used to assess the MV parameters, by including the structural simulation with FEA it is possible to also simulate the changes in airway structure thereby improved further the parameter optimisation. It is understood the subject's respiratory system may remodel during the course of MV treatment. Therefore, the MV settings may be further be optimised after treatment has begun, by periodically repeating method of the invention.

When the invention is applied to determine the efficacy of treatment, separate flow simulations are made based on the models obtained prior to and after the start of treatment. The simulations are compared to determine progress of the condition and the effectiveness of treatment. Generally, an efficacious treatment is one that decreases the airway resistance thereby increasing the lobar mass flow for the same driving pressure.

Using the present invention the patient can be treated using a minimal number of invasive step. The subject requiring MV undergoes a CT or MRI scan prior to treatment. Subsequently the scan data is transferred to the MV device which reads in the CT/MRI images, creates a patient-specific three-dimensional model of the airway system, lungs and lobes. Then the device performs flow and/or structural simulations at different pressure settings. The mass flow rate distribution is monitored and the optimal parameters are selected for the patient.

Alternatively, using the present invention, the subject being treated for a respiratory-type condition undergoes a CT or MRI scan prior to treatment and a CT or MRI after the start of treatment (e.g. at 1, 2, 3, 4, 5, 6, 7, 8, 9, 10, 11, 12 month interval(s)). Subsequently the scan data is transferred to the MV device which reads in the CT/MRI images, creates a patient-specific three-dimensional model of the airway system, lungs and lobes. Then the device performs flow and/or structural simulations at different pressure settings. The mass flow rate distribution is determined prior to and after the start of treatment, and the efficacy of treatment is determined based on the observed changes in flow rate distribution.

One embodiment of the present invention is a computer program stored on a computer readable medium configured to perform a method of the invention.

Another embodiment of the invention is a flow model obtained using a method of the present invention.

Another embodiment of the present invention is a use of a flow model obtained according to the invention for determining optimized MV parameters, or efficacy of treatment.

EXAMPLES

Clinical Study: Non-Invasive Ventilation in COPD Patients

In order to demonstrate the effect of MV in chronic obstructive pulmonary disease (COPD) patients, a clinical study was designed. In this study 20 patients were included after an exacerbation of the symptoms. In a control group, 10 patients were treated using inhalation medication only. In an experimental group, 10 other patients received, in addition to the inhalation medication, nocturnal sessions of Bi-level Positive Airway Pressure (BiPAP)—an NIV treatment. Patients were evaluated after 6 months to assess the effect of both methods, and again after 12 months when all MV activities were stopped. This study functions as the basic validation to develop the method to determine optimal ventilation parameters.

Preliminary Results: Non Invasive Ventilation in COPD Patients

FIGS. 5-9 show the initial results for patient 1 (control), and patients 2 to 5 (NIV-treated). These data indicate that for both the actively treated patients and the control patients, a change in resistance and flow distributions can be observed over the 6 month period. However, the changes in the control patients are more homogenous. This indicates that the NIV method induces a different remodeling pattern due to the additional pressure. FIG. 10 shows contours of static pressure for a patient specific airway model, wherein regions of common shading have the same static pressure. As explained in the previous sections, these static pressure generate a mass flow, at baseline, towards the lobes proportional to the lobar growth as derived from the CT data. When the pressures at the bronchioli are kept the same and the mouth or tracheal pressure is augmented up to the level of the MV, the change in mass flow rate can be observed and analysed. FIG. 11 illustrates this by assessing the changes in lobar mass flow distribution as a function of different Peak End Expiratory Pressures (PEEP). PEEP is one of the parameters that can be set in a MV device. For this patient it can be seen that the main effect can be found in the upper lobes (RUL, LUL) with a shift in mass flow distribution from the right upper lobe (RUL) to the left (LUL) as the PEEP increases.

Clinical Study: IPV in COPD Patients

In this study, the effect of Intrapulmonary percussive ventilation (IPV) on mucus clearance is investigated in five COPD patients. A baseline CT scan of the COPD patient was taken at the first visit together with all classic lung function test (spirometry & body plethysmography). Subsequently, the patient was treated twice for 10 minutes with a break of 5 minutes. The IPV pressure was set at 2.5 bar and the IPV frequency was 350 cycles/min. After the treatment a second scan was taken. Both scans were segmented and flow simulations were performed to assess the change in resistance as described in the previous sections.

Preliminary Results: IPV in COPD Patients

FIGS. 12-14 show the first results for the assessment of the IPV effect on airway geometry and also resistance for one patient. In FIG. 12, the circled regions indicate differences in airway morphology before (FIG. 12A) and after (FIG. 12B) treatment in patient 1. Differences in flow resistance calculated according to the method before and after treatment are tabulated in (FIG. 12C). FIG. 13A shows the lobar segments of the lung of patient 2 from the frontal view, and FIG. 13B depicts some of the airways through a cut-away part. Circled regions indicate differences in this airway morphology before (FIG. 13C) and after (FIG. 13D) treatment. FIG. 14 shows differences in this airway morphology in patient 3 before (FIG. 14A) and after (FIG. 14B) treatment. From these images it is clear that functional imaging with CFD can indeed identify the changes induces by the IPV method while the classic outcome parameters (FEV1, FVC and Tiffeneau) remained unchanged. In addition the changes in geometry and resistance can be quantified and correlated with the patient's condition.

CONCLUSIONS

Functional imaging using computer methods provides a more detailed view of the patient's condition. Initial studies using NIV and IPV have indicated that changes in the respiratory system can be analysed using this method with a high degree of accuracy. The validated approach is then expandable to simulate more scenarios with different MV settings. The patient-specific response to these changes can be assessed and the optimal parameters can be selected.

What is claimed is:

1. A method for assessing an efficacy of a treatment for a respiratory condition in a subject comprising the steps of:
   a) obtaining data concerning a pre-treatment three-dimensional image of a respiratory system of the subject, and a post-treatment three-dimensional image of the respiratory system of the subject,
   b) calculating a specific three-dimensional structural model of a lung structure of the subject from each of the pre- and post-treatment image data obtained in step a),
   c) calculating a specific three-dimensional structural model of an airway structure of the subject from each of the pre- and post-treatment image data obtained in step a),
   d) calculating a patient-specific three-dimensional structural model of a lobar structure of the subject from each of the pre- and post-treatment lung structure models obtained in step b),
   e) modeling by a computer, air flow through the airway structure at pre- and post-treatment states, using the respective pre- and post-treatment models of the airway structure and lobar structure of the subject obtained in steps c) and d);
f) modeling by a computer, structural behavior of the airway structure and the interaction with the air flow at pre- and post-treatment states, using the respective pre- and post-treatment models of the airway structure and lobar structure of the subject obtained in steps c) and d);
g) comparing the modeled air flow pre- and post-treatment and comparing the structural behaviour pre- and post-treatment to determine the efficacy of the treatment, wherein an efficacious treatment is one that decreases airway resistance, thereby increasing lobar mass for a same driving pressure, thereby determining the efficacy of the treatment for the respiratory condition.

2. Method according to claim 1, wherein an increased efficacy is further defined by an increase in mass flow rate towards well-perfused areas.

3. Method according to claim 1, wherein the image data of step a) is computed tomography (CT) or magnetic resonance imaging (MRI) scan data.

4. Method according to claim 1, wherein the structural model of step c) is calculated using segmentation principles.

5. Method according to claim 1, wherein the model of the lobar structure of step d) is calculated using lobar segmentation.

6. Method according to claim 1, wherein the modeling of step e) comprises computational fluid dynamics incorporating solving Navier-Stokes equations numerically.

7. Method according to claim 6, wherein the model of the lobar structure calculated in step d) is used to determine boundary conditions for computational fluid dynamics.

8. Method according to claim 7, wherein
the data of step a) concerns three dimensional images of the respiratory system at total lung capacity (TLC) and at functional residual capacity (FRC),
the model of the lung structure in step b) and the model of the lobar structure in step d) are calculated both at TLC and FRC,
to determine mass flow rate towards each lobe and subsequently the boundary conditions for said computational fluid dynamics.

9. Method according to claim 1, wherein the modeling of step f) comprises Finite Element Analysis.

10. A non-transitory computer-readable medium comprising a computer program comprising computer executable instructions that, when executed by a computing device, configure the computing device to perform operations comprising:
a) obtaining data concerning a pre-treatment three-dimensional image of a respiratory system of the subject, and a post-treatment three-dimensional image of the respiratory system of the subject;
b) calculating a specific three-dimensional structural model of a lung structure of the subject from each of the pre- and post-treatment image data obtained in step a);
c) calculating a specific three-dimensional structural model of an airway structure of the subject from each of the pre- and post-treatment image data obtained in step a);
d) calculating a patient-specific three-dimensional structural model of a lobar structure of the subject from each of the pre- and post-treatment lung structure models obtained in step b);
e) modeling by a computer, air flow through the airway structure at pre- and post-treatment states, using the respective pre- and post-treatment models of the airway structure and lobar structure of the subject obtained in steps c) and d);
f) modeling by a computer, structural behavior of the airway structure and the interaction with the air flow at pre- and post-treatment states, using the respective pre- and post-treatment models of the airway structure and lobar structure of the subject obtained in steps c) and d); and
g) comparing the modeled air flow pre- and post-treatment and comparing the structural behaviour pre- and post-treatment to determine an efficacy of a treatment, wherein an efficacious treatment is one that decreases airway resistance, thereby increasing lobar mass for a same driving pressure, thereby determining the efficacy of the treatment for the respiratory condition.

* * * * *

UNITED STATES PATENT AND TRADEMARK OFFICE
CERTIFICATE OF CORRECTION

| | | |
|---|---|---|
| PATENT NO. | : 8,886,500 B2 | Page 1 of 1 |
| APPLICATION NO. | : 13/322104 | |
| DATED | : November 11, 2014 | |
| INVENTOR(S) | : Jan De Backer | |

It is certified that error appears in the above-identified patent and that said Letters Patent is hereby corrected as shown below:

Specification

In column 1 at line 27, Change "(NW)." to --(NIV).--.

In column 1 at line 28, Change "endrotracheal" to --endotracheal--.

In column 1 at line 28, Change "tracheotomy" to --tracheostomy--.

In column 1 at line 29, Change "NW" to --NIV--.

In column 1 at line 31, Change "tracheotomy" to --tracheostomy--.

In column 6 at line 8, Change "endrotracheal" to --endotracheal--.

In column 6 at line 8, Change "tracheotomy," to --tracheostomy,--.

Signed and Sealed this
Sixteenth Day of February, 2016

Michelle K. Lee
*Director of the United States Patent and Trademark Office*